United States Patent [19]

Kraus

[11] Patent Number: 5,415,617
[45] Date of Patent: May 16, 1995

[54] APPLICATOR COIL FOR MAGNETIC FIELD THERAPY

[76] Inventor: Werner Kraus, Augustenstrasse 41, 8000 Muenchen 2, Germany

[21] Appl. No.: 6,692

[22] Filed: Jan. 21, 1993

Related U.S. Application Data

[63] Continuation of Ser. No. 703,164, May 20, 1991, abandoned.

[30] Foreign Application Priority Data

May 29, 1990 [DE] Germany ................. 9006056 U

[51] Int. Cl.$^6$ .............................................. A61N 1/00
[52] U.S. Cl. ........................................ 600/13; 600/14; 600/15; 607/51; 336/90; 336/122; 336/230
[58] Field of Search ................. 600/9, 13–15; 604/20; 606/23; 607/51, 115, 154, 103, 104; 128/862, 24.1, 792, 793; 336/230, 231, 227, 225, 90, 122; 219/10.79, 10.81, 10.75, 10.57; 335/214, 299; 34/96, 97, 99

[56] References Cited

U.S. PATENT DOCUMENTS

| 2,432,194 | 12/1947 | Hanchett | 336/90 |
| 2,580,293 | 12/1951 | Gier et al. | 336/227 |
| 3,915,151 | 10/1975 | Kraus | 600/13 |
| 4,066,065 | 1/1978 | Kraus | 600/13 |
| 5,116,304 | 5/1992 | Cadwell | 600/13 |
| 5,195,941 | 3/1993 | Erickson et al. | |

FOREIGN PATENT DOCUMENTS

| 2116869 | 7/1987 | Germany . |
| 1918299 | 10/1990 | Germany . |
| 0283236 | 1/1928 | United Kingdom . |
| 2132486 | 7/1984 | United Kingdom . |
| 2217990 | 11/1989 | United Kingdom . |

Primary Examiner—Lee S. Cohen
Assistant Examiner—Brian L. Casler
Attorney, Agent, or Firm—Iandiorio & Teska

[57] ABSTRACT

Applicator coil for an electromagnetic therapy apparatus, which has substantially the form of a zone of a sphere deformed into an oval and which is suited above all to rendering a low frequency magnetic alternating field operative on projecting parts of the human or animal body, such as the shoulder region or the face of the person.

8 Claims, 2 Drawing Sheets

APPLICATOR COIL FOR MAGNETIC FIELD THERAPY

This is a continuation of application Ser. No. 07/703,164, filed May 20, 1991 now abandoned.

BACKGROUND OF THE INVENTION

(1) Field of the Invention

The present invention relates to an applicator coil for magnetic field therapy.

(2) Description of the Prior Art

From U.S. Pat. No. 4,066,065 there is known an applicator coil in the form of a multi-layer cylinder or solenoid coil with an oval or elliptical cross-section.

The applicator coils of the kind of interest here serve for healing treatment by means of low frequency magnetic fields, whose frequencies preferably lie below 20 Hz, in human and veterinary medicine. The magnetic field should be as closely as possible sinusoidal; it can serve directly for treatment or for induction of low frequency alternating currents in an implanted receiver coil, which forms a part of a device for promoting the growth of bones or tissue (see e.g. U.S. Pat. Nos. 3,754,995 and 3,890,953, incorporated by reference).

The known hollow cylindrical applicator coils serve first and foremost for treating extremities or the trunk and are pushed over the part to be treated for this purpose. They are however not very well suited to selective treatment of projecting parts of the body, such as a shoulder or the facial region.

SUMMARY OF THE INVENTION

The present invention is accordingly based on the problem of providing an applicator coil for the generation of a low frequency magnetic field for an electromagnetic therapy apparatus, which is suited especially to the selective treatment of projecting parts of the human body and, if desired the animal body.

This problem is solved by an applicator coil which has essentially the form of a zone of a sphere deformed into an oval.

Developments and advantageous embodiments of the applicator coil according to the invention are the subject matter of the claims.

In that the applicator coil has substantially the form of a zone of a sphere deformed to an oval or like a trapezium with rounded ends, that is to say cup-like with a cross-section which reduces from a larger opening to a smaller opening, it can be applied closely to a projecting part of the body, such as the face or a shoulder, whereby effective treatment is ensured.

The preferred development of the present applicator coil is to provide it internally with spray nozzles, through which a treatment fluid, such as a liquid spray or a gas can be rendered active on the surface of the body part being treated.

BRIEF DESCRIPTION OF THE DRAWINGS

A preferred embodiment of the invention is described in more detail below with reference to the drawings. These show.

DESCRIPTION OF THE PREFERRED EMBODIMENT

Figure 1:
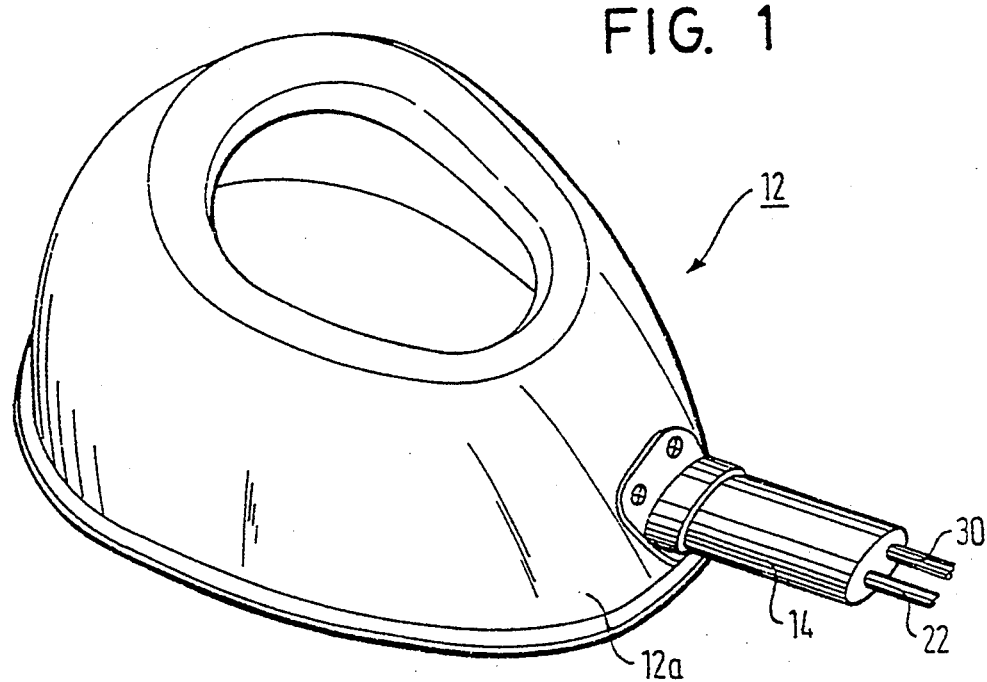
FIG. 1 a perspective view of the outside of an applicator coil according to a preferred embodiment of the invention.
Figure 2:
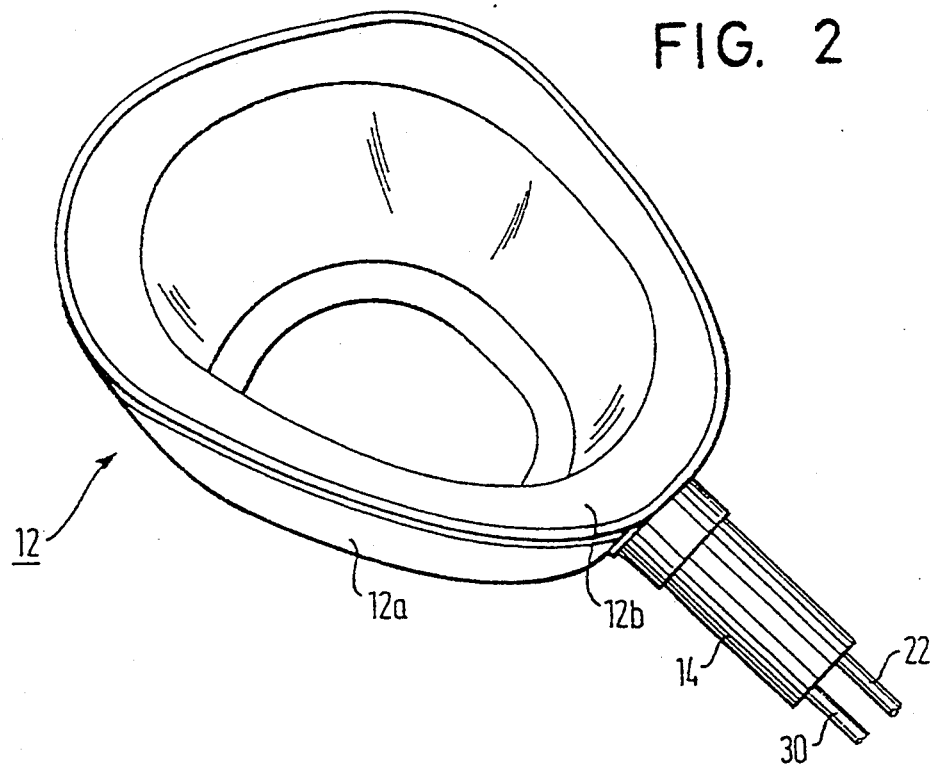
FIG. 2 a perspective view of the inside of the applicator coil according to FIG. 1 and FIG. 3 a somewhat simplified longitudinal section of the applicator coil according to FIGS. 1 and 2.

The applicator coil shown in the drawings has approximately the form of a zone of a sphere deformed like an egg or an oval. It includes a correspondingly deformed multi-layer wire winding 10, whose turns are substantially egg-shaped or have the form of trapezia with rounded ends. The winding density can be somewhat greater at the wider end than at the narrower end of the coil. The winding 10 is enclosed in a plastics casing 12, which consists of two shells 12a, 12b which have flange-like edges 15, 16, which are bonded or welded together. At the narrower or sharper end of the outer shell 12a there is fitted a handle 14. The applicator coil has a narrower opening 18, which is bounded by a rounded part of the outer shell 12a. At the wider end 20 the applicator coil is substantially flat up to the flange 15. The coil winding 10 is provided with terminals 21, which are fitted in the handle 14 and are connected to a connecting cable 22, with which the applicator coil can be connected to a generator unit for generating a low frequency, sinusoidal alternating current, the frequency of which is preferably variable between around 2 and 20 Hz.

According to the preferred arrangement the applicator coil is provided with a device for feeding a treatment fluid. To this end it has openings or nozzles 24 formed through the inner shell 12b, which are connected via branch lines 26 to a feed line 38, to which there is further connected a hose 30. The hose 30 is connected to a source of a liquid or a gaseous treatment medium during use of the applicator coil and permits the magnetic field treatment to be assisted by an application of a suitable fluid, such as a healing medium or cosmetic agent, to the surface of the body part being treated.

Figure 3:
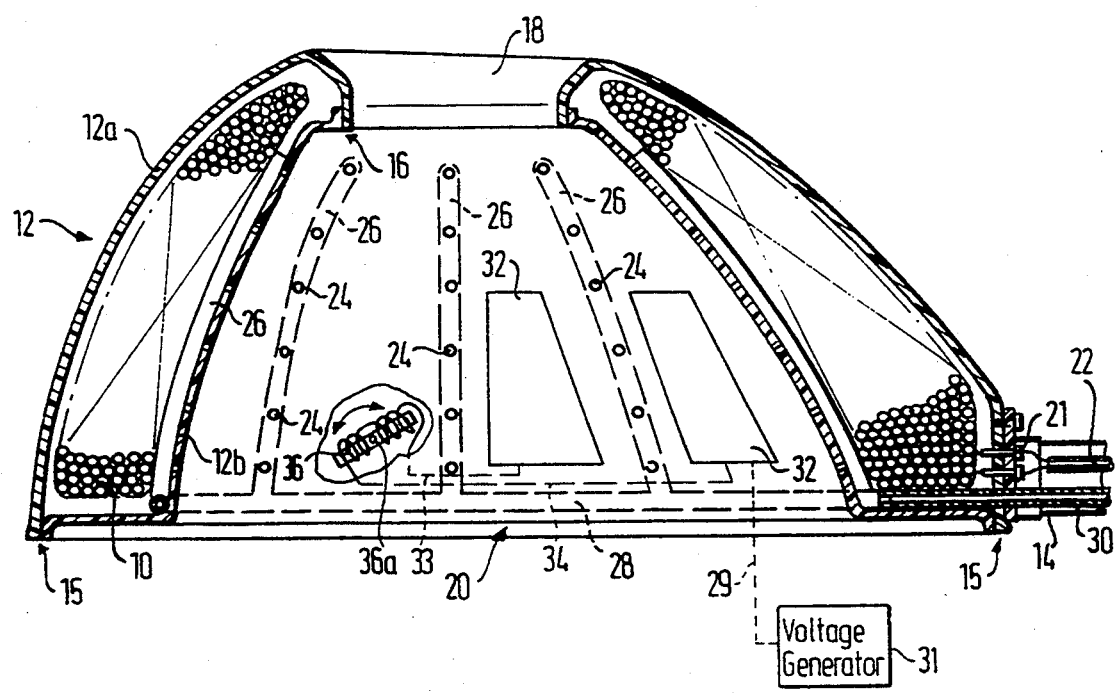

Electrodes 32 can be provided on the inside of the plastics casing 12, with which an electric field can be caused to act on the body part to be treated, either galvanically or capacitively. These electrodes can be capable of connection through their own lead to a suitable generator 31 for an alternating voltage either symmetrical or asymmetrical relative to zero or a unipolar voltage with low frequency fluctuations, i.e. a DC voltage on which an alternating voltage is superimposed, or can be connected to their own receiver coil 36 (FIG. 3) via lines 32, 34, in which a corresponding low frequency voltage can be induced through the winding 10. This receiver coil can be rotatably arranged in the plastics casing 12 such as by pin 36a, in order to be able to adjust the intensity and/or phase angle of the induced alternating voltage and be coupled to a rectifier circuit if desired, in order to generate an alternating voltage asymmetrical with respect to zero or a fluctuating unipolar voltage for the electrodes.

I claim:

1. An applicator coil for an electromagnetic therapy apparatus comprising:

coil windings; and shell means for enclosing said windings wherein said shell means have an inner shell with a plurality of orifices therethrough and an outer shell spaced from said inner shell.

2. The applicator coil of claim 1 in which said coil windings are within said space between said inner and outer shells.

3. The applicator coil according to claim 1 wherein the coil has a wider end and a narrower end and the density of the winding is greater at the wider end of the applicator coil than at the narrower end.

4. The applicator coil according to claim 1 further including fluid feeding means for feeding fluid through said orifices of said inner shell.

5. The applicator coil of claim 1 further including electrodes arranged on an inside of said inner shell.

6. The applicator coil of claim 5 further including voltage generation means for generating a voltage in which said electrodes are connected to said voltage generation means.

7. The applicator coil of claim 1 further including a receiver coil disposed within said shell means.

8. The applicator coil of claim 7 further including means to rotate said receiver coil.

* * * * *